United States Patent [19]
Dubois et al.

[11] Patent Number: 4,770,810
[45] Date of Patent: Sep. 13, 1988

[54] ORGANIC COMPOUND HAVING A SMECTIC PHASE A, AND A MIXTURE COMPRISING THIS COMPOUND

[75] Inventors: Jean C. Dubois, Saint Remy Les Chevreuses; Gilles Ravaux, Les Ulis; Pierre Le Barny, Orsay, all of France

[73] Assignee: Thomson-CSF, Paris, France

[21] Appl. No.: 795,432

[22] Filed: Nov. 6, 1985

[30] Foreign Application Priority Data

Nov. 9, 1984 [FR] France ................... 84 17111

[51] Int. Cl.$^4$ ............ C09K 19/30; C07C 121/52
[52] U.S. Cl. ............ 252/299.63; 252/299.01; 350/3505; 558/416
[58] Field of Search ............ 558/416; 252/299.63

[56] References Cited

U.S. PATENT DOCUMENTS 4,212,762 7/1980 Dubois et al. ............ 558/416

FOREIGN PATENT DOCUMENTS 3339216 5/1984 Fed. Rep. of Germany .
2573086 5/1986 France ............ 558/416
2123409 2/1984 United Kingdom .

OTHER PUBLICATIONS

French Search Report, Jun. 28, 1985, No. FA 356 224.

*Primary Examiner*—Anton H. Sutto
*Attorney, Agent, or Firm*—Oblon, Fisher, Spivak, McClelland & Maier

[57] ABSTRACT

The invention relates to a family of organic compounds of the 1(4 hydroxyphenyl)2(4' cyanophenyl) ethane ester type which have a smectic A type mesomorphic phase, to the mixture obtained from these compounds as well as the method for manufacturing the molecules of this family. The compound of the invention corresponds to the general chemical formula:

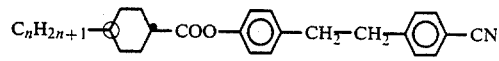

n being between 1 and 15.

14 Claims, 1 Drawing Sheet

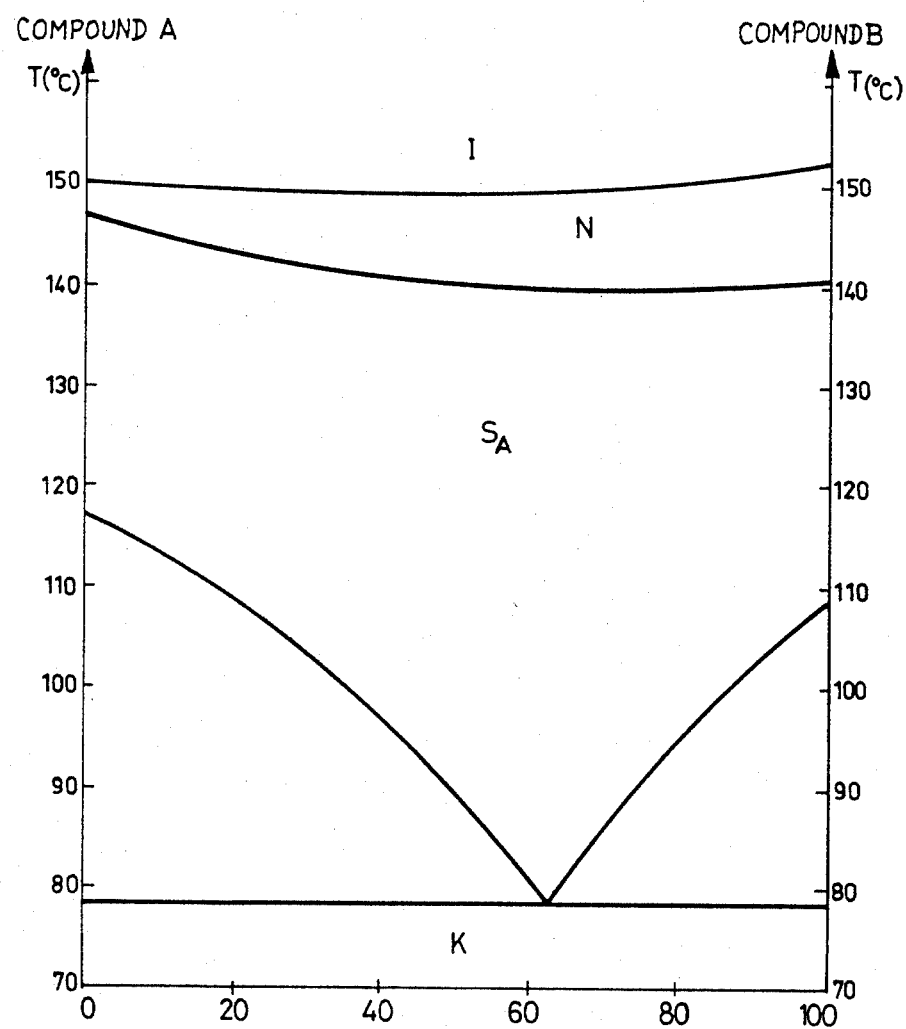

ORGANIC COMPOUND HAVING A SMECTIC PHASE A, AND A MIXTURE COMPRISING THIS COMPOUND

BACKGROUND OF THE INVENTION

1. Field of the Invention

The invention relates to a family of organic compounds of the 1-(4 hydroxyphenyl)2-(4'cyanophenyl)ethane ester type which has a type A smectic mesophase and possibly a nematic mesophase. The invention also relates to the method of manufacturing the molecules of this family, as well as the mixtures obtained from these esters and also having a smectic phase A.

2. Description of the Prior Art

In the prior art there exists a whole range of liquid crystals having a smectic phase A. They generally have a fairly limited mesomorphic range. To overcome these disadvantages, the invention proposes organic compounds for obtaining much larger ranges.

The compounds of the invention have the property, when they are mixed with smectic A liquid crystals, of widening the smectic range which these products present. This is an advantage when such mixtures are used in display devices whose range of use is extended towards both high and low temperatures.

SUMMARY OF THE INVENTION

The compounds of the invention correspond to the general chemical formula:

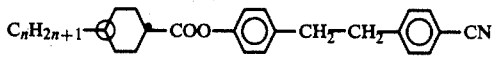

with $1 \leq n \leq 15$.

The symbol

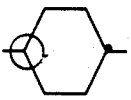

relates to a derivative of para disubstituted cyclohexane, the substituents being in an equatorial position which leads to trans derivatives.

The compounds corresponding to this formula may be defined by the following denomination: 1-(4 alkyl cyclohexyl carbonyloxyphenyl) 2-(4'cyanophenyl)ethane.

The invention provides then an organic compound having at least one mesomorphic phase of smectic A type corresponding to the general chemical formula:

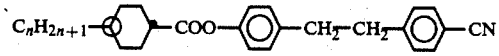

in which $1 \leq n \leq 15$.

The invention also relates to a mixture of liquid crystals having at least one smectic A phase, comprising at least one of the above mentioned organic compounds.

A further object of the invention is a process for manufacturing a compound such as mentioned above, in which said compound is a product of the reaction of acid chloride

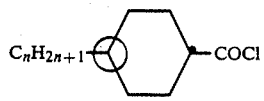

and phenol

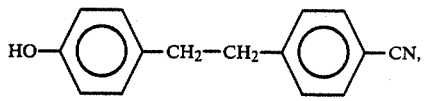

said reaction taking place at ambient temperature in pyridine.

BRIEF DESCRIPTION OF THE DRAWING

The invention will be better understood and other advantages will be clear from the following description and accompanying FIGURE which shows an isobar phase diagram.

DESCRIPTION OF THE PREFERRED EMBODIMENTS

The following description will relate to the general method for synthesizing the molecules of the invention, as well as to the mesomorphic properties of the corresponding liquid crystals. In addition, an example of incorporating a compound of the invention in a smectic A material intended for display purposes using a mixed thermal and electric effect, will show the widening of the range of use of this display to low and high temperatures.

General synthesis method

The organic compounds of the invention may be obtained in 9 steps for $n \geq 9$ from the following commercial products: 4 bromo-phenylacetic acid, methoxybenzene and alkyl benzene or in 7 steps for $n \leq 8$ for in this case the alyl benzoic acids are available commercially.

Reaction 1: Obtaining 4 bromophenylacetyle chloride. This acid chloride is obtained by reacting thionyl chloride on 4 bromophenylacetic acid.

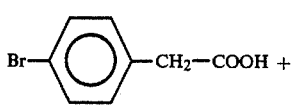

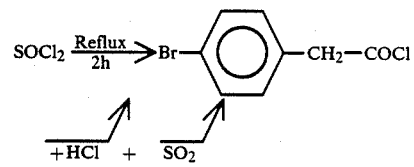

Reaction 2: synthesis of 4-(4bromophenylacetyl)4'-methoxyphenyl. 4-(4 bromophenylacetyl)4'methoxyphenyl is obtained by reacting 4 bromophenylacetyl chloride on methoxybenzene in the presence of aluminium chloride and methylene chloride, at a temperature of 5° C. (FRIEDEL-CRAFT Reaction).

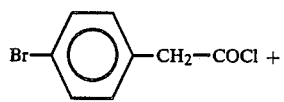

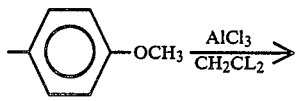

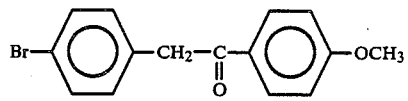

Reaction 3: obtaining 1-(4 bromophenyl)2-(4'hydroxyphenyl)ethane. 4-(4 bromophenylacetyl) 4'-methoxyphenyl is reduced into 1-(4 bromophenyl) 2-(4'hydroxyphenyl)ethane in accordance with the WOLF-KISHNER reaction modified by HUANG-MINLON, by reacting hydrazine in a basic medium and in the presence of diethylene glycol. The basic medium is obtained by potash. This reaction is accompanied by a total cut off of the ether function.

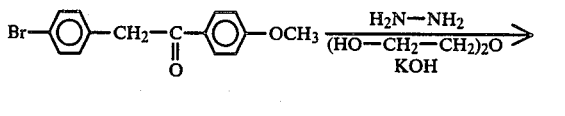

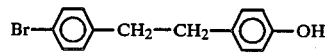

The phenol thus obtained is purified by transforming it into acetate by means of acetyl chloride in the presence of pyridine. The acetate is chromatographed on silica with toluene as eluent, then saponified in an alcohol potash medium. Which leads to potassium phenate which is transformed into phenol by reaction with hydrochloric acid.

Reaction 4: synthesis of 1-(4 cyanophenyl) 2-(4'hydroxyphenyl)ethane.

1-(4 cyanophenyl) 2-(4'-hydroxyphenyl)ethane is obtained by cyanuration of 1-(4 bromophenyl) 2-(4'hydroxyphenyl)ethane by means of copper cyanide using N methyl pyrrolidone as solvent.

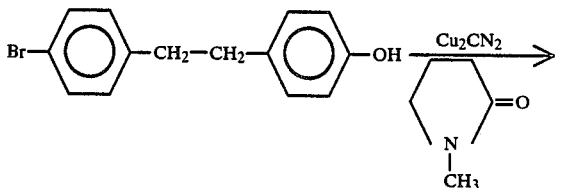

Reaction 5: obtaining 4 alkyl 4'acetyl phenyl.

4 alkyl 4' acetyl phenyl is obtained by reacting acetyl chloride on benzene alkyl in the presence of aluminium chloride and carbon tetrachloride at 5° C. (FRIEDEL-CRAFT Reaction).

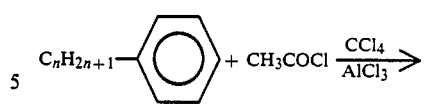

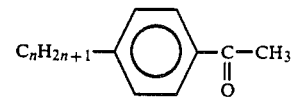

Reaction 6: synthesis of the 4 alkyl benzoic acids.

The 4 alkyl benzoic acids are obtained by oxidation of 4 alkyl 4'acetyl phenyls using sodium hypobromite. The resulting sodium salt is acidified by hydrochloric acid.

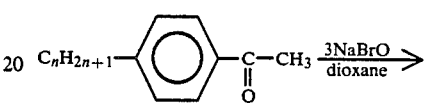

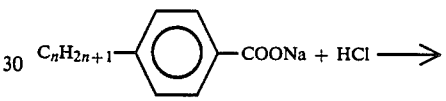

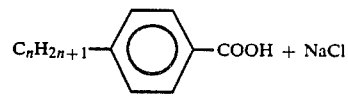

Reaction 7: obtaining trans 4 alkyl cyclohexane carboxylic acid. By hydrogenating 4 alkyl benzoic acids at 200° C., at a pressure of 200 bars in the presence of Raney Nickel W2 and in a basic medium, a cis-trans mixture of 4 alkyl cyclohexane carboxylic acid is obtained rich in trans isomer.

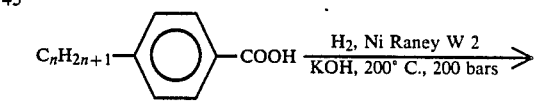

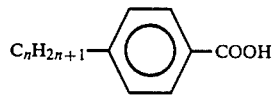

The trans isomere is separated from the mixture by formation of an inclusion compound with thiourea.

Reaction 8: synthesis of the trans 4 alkyl cyclohexane carbonyloxy chlorides.

The acid chlorides are obtained by reacting thionyl chloride on the trans 4 alkyl cyclohexane carboxylic acids.

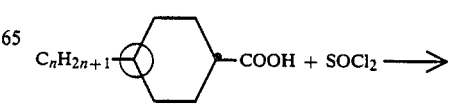

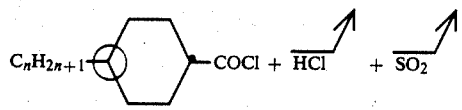

Reaction 9: synthesis of 1-(4 alkylcyclohexylcarbonyloxyphenyl) 2-(4′ cyanophenyl)ethanes.

These esters are synthesized from acid chloride

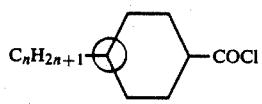

and from phenol

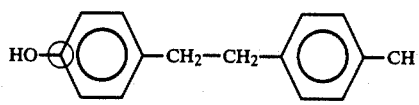

obtained by reaction 4, at the ambient temperature in the presence of pyridine.

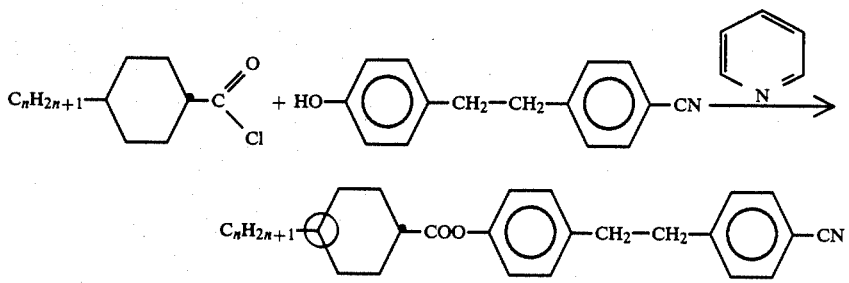

The mode of operation which has just been described is valid whatever the values of n provided that the molar proportions are respected.

The compounds of the invention correspond to the following denominations:

1-(4 methyl cyclohexyl carbonyloxyphenyl) 2-(4′cyanophenyl)ethane.
1-(4 ethyl cyclohexyl carbonyloxyphenyl) 2-(4′ cyanophenyl)ethane.
1-(4 propyl cyclohexyl carbonyloxyphenyl)2-(4′ cyanophenyl)ethane.
1-(4 butyl cyclohexyl carbonyloxyphenyl)2-(4′ cyanophenyl)ethane.
1-(4 pentyl cyclohexyl carbonyloxyphenyl) 2-(4′ cyanophenyl)ethane.
1-(4 hexyl cyclohexyl carbonyloxyphenyl)2-(4′ cyanophenyl)ethane.
1-(4 heptyl cyclohexyl carbonyloxyphenyl)2-(4′ cyanophenyl)ethane.
4-(4 octyl cyclohexyl carbonyloxyphenyl)2-(4′ cyanophenyl)ethane.
1-(4 nonyl cyclohexyl carbonyloxyphenyl)2-(4′ cyanophenyl)ethane.
1-(4 decyl cyclohexyl carbonyloxyphenyl)2-(4′ cyanophenyl)ethane.
1-(4 undecyl cyclohexyl carbonyloxyphenyl)2-(4′ cyanophenyl)ethane.
1-(4 dodecyl cyclohexyl carbonyloxyphenyl)2-(4′ cyanophenyl)ethane.
1-(4 tridecyl cyclohexyl carbonyloxyphenyl) 2-(4′ cyanophenyl)ethane.
1-(4 tetradecyl cyclohexyl carbonyloxyphenyl)2-(4′ cyanophenyl)ethane. and
1-(4 pentadecyl cyclohexyl carbonyloxyphenyl)2-(4′ cyanophenyl)ethane.

Properties of the synthesized substances

By way of non limitative example, the calorimetric analysis associated with the contact method allowed the following characteristics to be determined for the ester of the invention corresponding to n=9. This ester has the following phase transitions:

K117.4° C.[5.5]$S_A$147.6° C.[0.14]N150.3° C.[0.8]I

The letters K, $S_A$, N and I designate respectively the crystalline, smectic A, nematic and isotropic phases. The values between brackets are the transition enthalpies expressed in Kcal/mole.

The nature of the mesophases was determined by studying with the optical microscope the isomorphism of the compounds studied with known substances. By way of example, the accompanying FIGURE shows an isobar phase diagram obtained by contacting 1(4 nonyl cyclohexyl carbonyloxyphenyl)2-(4′ cyanophenyl)ethane (or compound 1), of the invention with a product of the substitued 2 hydroxyfluorene ester type of formula:

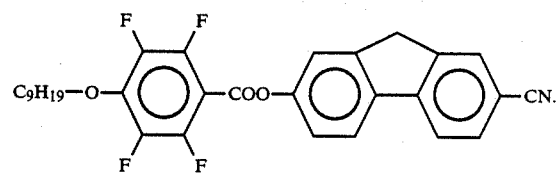

(or compound B). Compound B has the following succession of phases:

K109° C. $S_A$140.5° C. N152.5° C. I

This ester is described in the French patent application of the applicant published under the No. FR-A-2.538.804. In the diagram, the left hand ordinate axis corresponds to 100% of compound A whereas that at the right corresponds to 100% of compound B. The ordinate axes are graduated in degrees Celsius, the abscissa axis corresponds to the percentage of compound B in the mixture.

Whatever the proportions of compounds A and B in the mixture, this latter still has a succession of phases crystalline-smectic A-nematic-isotropic.

Without departing from the scope of the invention, the organic compounds of the invention can be used as liquid crystals having a smectic A phase, alone, mixed together or with other smectic A liquid crystals, so as to extend the temperature range in use. Thus, they may be advantageously used in display devices.

The following example shows the influence of introducing a compound in accordance with the invention into a mixture of two liquid crystals called compounds C and D. Compound C is 4 octyl 4' cyanobiphenyl of formula

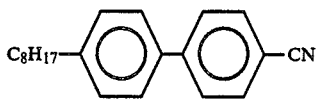

which has the following phase transitions: K 21.5° C. $S_A$ 33.5° C. N 40.5° C. I. The compound D is 4 decyl 4' cyanobiphenyl of formula:

which has the following phase transitions K 43.5° C. $S_A$ 51° C. I. The eutectic formed from compounds C and D has a melting point of 13° C., a smectic A—nematic transition at 38.1° C. and a clarification temperature of 43.3° C. so a mesomorphic range of 30.3° C.

The introduction of 1-(4 nonyl cyclohexylcarbonyloxyphenyl) 2-(4' cyanophenyl)ethane leads to a ternary eutectic comprising 63.2% of compound C, 21.4% of compound D and 15.4% of ester in accordance with the invention. This eutectic has a melting point of 8.9° C., a smectic A-nematic transition temperature of 63.4° C. and a clarification temperature of 68.6° C. The mesomorphic range of this ternary mixture extends then over 59.7° C. With respect to the above described binary mixture it can be seen that the mesomorphic range is more extensive and that the limit temperatures of this range has been pushed back towards the low and high temperatures.

What is claimed is:

1. A mixture of liquid crystals having at least a smectic A phase, comprising 4-octyl-4'-cyanobiphenyl, 4-decyl-4'-cyanobiphenyl, and one compound of the general chemical formula:

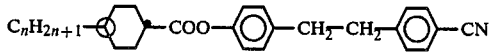

in which $1 \leq n \leq 15$.

2. The mixture of claim 1, comprising 1-(4-methylcyclohexylcarbonyloxyphenyl)-2-(4'-cyanophenyl)ethane; 1-(4-ethylcyclohexylcarbonyloxyphenyl)-2-(4'-cyanophenyl)ethane; or 1-(4-propylcyclohexylcarbonyloxyphenyl)-2-(4'-cyanophenyl)ethane.

3. The mixture of claim 1, comprising 1-(4-butylcyclohexylcarbonyloxyphenyl)-2-(4'-cyanophenyl)ethane; 1-(4-pentylcyclohexylcarbonyloxyphenyl)-2-(4'-cyanophenyl)ethane; or 1-(4-hexylcyclohexylcarbonyloxyphenyl)-2-(4'-cyanophenyl)ethane.

4. The mixture of claim 1, comprising 1-(4-heptylcyclohexylcarbonyloxyphenyl)-2-(4'-cyanophenyl)ethane; 1-(4-octylcyclohexylcarbonyloxyphenyl)-2-(4'-cyanophenyl)ethane; or 1-(4-nonylcyclohexylcarbonyloxyphenyl)-2-(4'-cyanophenyl)ethane.

5. The mixture of claim 1, comprising 1-(4-decylcyclohexylcarbonyloxyphenyl)-2-(4'-cyanophenyl)ethane; 1-(4-undecylcyclohexylcarbonyloxyphenyl)-2-(4'-cyanophenyl)ethane; or 1-(4-dodecylcyclohexylcarbonyloxyphenyl)-2-(4'-cyanophenyl)ethane.

6. The mixture of claim 1, comprising 1-(4-tridecylcyclohexylcarbonyloxyphenyl)-2-(4'-cyanophenyl)ethane; 1-(4-tetradecylcyclohexylcarbonyloxyphenyl)-2-(4'-cyanophenyl)ethane; or 1-(4-pentadecylcyclohexylcarbonyloxyphenyl)-2-(4'-cyanophenyl)ethane.

7. The mixture of claim 1, comprising about 63.2% of 4-octyl-4'-cyanobiphenyl, about 21.4% of 4-decyl-4'-cyanobiphenyl, and about 15.4% of said compound of the general chemical formula:

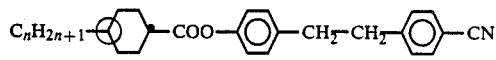

wherein $n = 9$.

8. An organic compound having at least one mesomorphic smectic A type phase, corresponding to the general chemical formula:

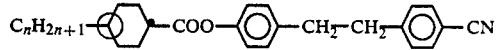

in which $1 \leq n \leq 15$.

9. The organic compound as claimed in claim 8, wherein $n = 9$.

10. The organic compound of claim 8, said compound being 1-(4-methylcyclohexylcarbonyloxyphenyl)-2-(4'-cyanophenyl)ethane; 1-(4-ethylcyclohexylcarbonyloxyphenyl)-2-(4'-cyanophenyl)ethane; or 1-(4-propylcyclohexylcarbonyloxyphenyl)-2-(4'-cyanophenyl)ethane.

11. The organic compound of claim 8, said compound being 1-(4-butylcyclohexylcarbonyloxyphenyl)-2-(4'-cyanophenyl)ethane; 1-(4-pentylcyclohexylcarbonyloxyphenyl)-2-(4'-cyanophenyl)ethane; or 1-(4-hexylcyclohexylcarbonyloxyphenyl)-2-(4'-cyanophenyl)ethane.

12. The organic compound of claim 8, said compound being 1-(4-heptylcyclohexylcarbonyloxyphenyl)-2-(4'-cyanophenyl)ethane; 1-(4-octylcyclohexylcarbonyloxyphenyl)-2-(4'-cyanophenyl)ethane; or 1-(4-nonylcyclohexylcarbonyloxyphenyl)-2-(4'-cyanophenyl)ethane.

13. The organic compound of claim 8, said compound being 1-(4-decylcyclohexylcarbonyloxyphenyl)-2-(4'-cyanophenyl)ethane; 1-(4-undecylcyclohexylcarbonyloxyphenyl)-2-(4'-cyanophenyl)ethane; or 1-(4-dodecylcyclohexylcarbonyloxyphenyl)-2-(4'-cyanophenyl)ethane.

14. The organic compound of claim 8, said compound being 1-(4-tridecylcyclohexylcarbonyloxyphenyl)-2-(4'-cyanophenyl)ethane; 1-(4-tetradecylcyclohexylcarbonyloxyphenyl)-2-(4'-cyanophenyl)ethane; or 1-(4-pentadecylcyclohexylcarbonyloxyphenyl)-2-(4'-cyanophenyl)ethane.

* * * * *